(12) United States Patent
Schoultz et al.

(10) Patent No.: US 8,813,351 B2
(45) Date of Patent: Aug. 26, 2014

(54) APPARATUS AND METHOD FOR APPLYING DISCRETE PARTS TO A MOVING WEB

(75) Inventors: Adam Schoultz, Neenah, WI (US); Chadwick I. Romzek, Neenah, WI (US); Brian Rhodes, Larsen, WI (US); Jesse Sorenson, Neenah, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 205 days.

(21) Appl. No.: 13/331,656

(22) Filed: Dec. 20, 2011

(65) Prior Publication Data

US 2013/0152360 A1  Jun. 20, 2013

(51) Int. Cl.
*B23P 21/00* (2006.01)

(52) U.S. Cl.
USPC ............... 29/782; 29/779; 29/786; 29/413; 198/471.1; 198/379

(58) Field of Classification Search
USPC ............ 198/471.1, 689.1, 379; 156/569, 568, 156/567, 562, 560, 559, 539; 493/383
See application file for complete search history.

(56) References Cited

U.S. PATENT DOCUMENTS

| | | | |
|---|---|---|---|
| 4,608,115 A * | 8/1986 | Schroth et al. | 156/519 |
| 4,610,751 A | 9/1986 | Eschler | |
| 4,617,082 A | 10/1986 | Oshefsky et al. | |
| 4,726,876 A | 2/1988 | Tomsovic, Jr. | |
| 5,091,039 A | 2/1992 | Ujimoto et al. | |
| 5,104,116 A * | 4/1992 | Pohjola | 271/185 |
| 5,660,665 A * | 8/1997 | Jalonen | 156/163 |
| 5,716,478 A | 2/1998 | Boothe et al. | |
| 5,746,869 A | 5/1998 | Hayden et al. | |
| 5,759,340 A | 6/1998 | Boothe et al. | |
| 5,873,870 A | 2/1999 | Seitz et al. | |
| 6,139,004 A | 10/2000 | Couillard et al. | |
| 6,523,595 B1 | 2/2003 | Milner et al. | |
| 6,540,857 B1 | 4/2003 | Coenen et al. | |
| 6,599,384 B2 | 7/2003 | Milner et al. | |
| 6,620,276 B1 | 9/2003 | Kuntze et al. | |
| 6,656,312 B1 | 12/2003 | Schmitz et al. | |
| 6,722,494 B2 | 4/2004 | Nakakado | |
| 6,748,996 B2 | 6/2004 | Nakakado et al. | |
| 7,008,497 B2 | 3/2006 | Nakakado et al. | |
| 7,195,684 B2 | 3/2007 | Satoh | |
| 7,216,685 B2 | 5/2007 | Nakakado et al. | |

(Continued)

FOREIGN PATENT DOCUMENTS

WO  9965436 A1  12/1999

OTHER PUBLICATIONS

International Search Report and Written Opinion for Application No. PCT/IB2012/057039 dated Apr. 25, 2013; 9 pages.

*Primary Examiner* — Alexander P Taousakis
*Assistant Examiner* — Matthew P Travers
(74) *Attorney, Agent, or Firm* — Armstrong Teasdale LLP.

(57) ABSTRACT

Apparatus for separately conveying a plurality of discrete parts from a web and applying each of the discrete parts to a substrate includes a plurality of transfer pucks and a drive assembly. The drive assembly is configured to rotate each of the transfer pucks such that a plurality of pairs of discrete parts is applied to the web. Each applied pair of discrete parts includes a first discrete part and a second discrete part spaced a first distance from the first discrete part, wherein adjacent pairs of discrete pairs are spaced a second distance that is different from the first distance.

13 Claims, 9 Drawing Sheets

(56) References Cited

U.S. PATENT DOCUMENTS

| | | |
|---|---|---|
| 7,220,335 B2 | 5/2007 | Van Gompel et al. |
| 7,438,779 B2 | 10/2008 | Nakakado |
| 7,721,872 B2 | 5/2010 | Aoyama et al. |
| 7,975,584 B2 | 7/2011 | McCabe |
| 7,987,964 B2 | 8/2011 | McCabe |
| 2004/0122391 A1 | 6/2004 | Franklin |
| 2006/0157188 A1 | 7/2006 | Thorson et al. |
| 2007/0142805 A1 | 6/2007 | Gompel et al. |
| 2008/0196564 A1* | 8/2008 | McCabe .................. 83/23 |
| 2011/0212818 A1 | 9/2011 | Nakakado et al. |

* cited by examiner

APPARATUS AND METHOD FOR APPLYING DISCRETE PARTS TO A MOVING WEB

FIELD

The field of the invention relates generally to web treatment apparatus and more specifically to apparatus for applying discrete parts to a moving web and a method of using the apparatus.

BACKGROUND

Some people rely on disposable absorbent products in their everyday lives including, for example, disposable absorbent articles such as adult incontinence products, enuresis pants, training pants, and diapers. Many manufacturers of these absorbent articles seek to better meet the needs of users. For example, there is an ongoing need to improve fit, discretion, and leakage protection for many of these articles.

Some absorbent articles employ elasticization across the front and/or back of the article to keep the article snug against the wearer during use. Some of these articles employ a multiplicity of elastic strands within front and/or back waist panels of the article to provide the elasticization, while others employ elastomeric polymeric films, which are often sandwiched with one or more nonwoven layers.

Most absorbent articles include an absorbent member, constructed from wood pulp fluff, superabsorbent polymers, and/or other absorbent material to absorb fluids (e.g., urine) discharged by the user. The absorbent member is typically positioned in the crotch region of the article and extends forward and backward into the article's front and/or back regions. In some absorbent articles, the elastic members that extend across the front and/or back waist panels of the article overlap the absorbent member at various locations since the absorbent member extends forward/backward into the front/back waist regions of the article.

Some absorbent articles include refastenable seams disposed along the sides of the article to enable the wearer or a caregiver to remove the article by detaching the front region from the back region along the seams. Because the refastenble seams are located along the sides of the article, some wearers find the seams difficult to manipulate. Refastenable side seams can also be difficult for some caregivers of bedridden individuals to manipulate.

Thus, there remains a need for apparatus and processes of manufacturing articles that have refastenable side seams that are easy to manipulate.

SUMMARY

In one aspect, an apparatus for conveying a plurality of discrete parts web and applying each discrete part to a substrate generally comprises a plurality of transfer pucks and a drive assembly. Each transfer puck is adapted to convey the discrete parts from the web to the substrate. The drive assembly is configured to rotate each transfer puck such that a plurality of pairs of discrete parts is applied to the substrate. Each applied pair of discrete parts includes a first discrete part and a second discrete part spaced a first distance from the first discrete part, wherein adjacent pairs of discrete pairs are spaced a second distance that is different from the first distance.

In another aspect, an apparatus for conveying a plurality of discrete parts and applying each discrete part to a substrate generally comprises a plurality of transfer pucks and a drive assembly. Each transfer puck is adapted to convey the discrete parts from the web to the substrate. The drive assembly is configured to rotate each transfer puck to selectively adjust a rotational speed of each transfer puck such that a plurality of pairs of discrete parts is applied to the substrate. Each applied pair of discrete parts includes a first discrete part and a second discrete part spaced a first distance from the first discrete part, wherein adjacent pairs of discrete pairs are spaced a second distance that is different from the first distance.

In still another aspect, a method of applying a plurality of discrete parts to a substrate generally comprises directing a web including the plurality of discrete parts toward an apparatus for conveying each discrete part from the web and applying each discrete part to the substrate. The apparatus includes a plurality of transfer pucks rotatably coupled to a drive assembly. Each transfer puck is rotated such that each transfer puck conveys each discrete part from the web to the substrate. A plurality of pairs of discrete parts including a first discrete part and a second discrete part is applied to the substrate such that the applied second discrete part is spaced a first distance from the applied first discrete part, and adjacent applied pairs of discrete parts are spaced a second distance that is different from the first distance.

BRIEF DESCRIPTION OF THE DRAWINGS

Corresponding reference characters indicate corresponding parts throughout the drawings.

DETAILED DESCRIPTION OF THE DRAWINGS

Figure 1:
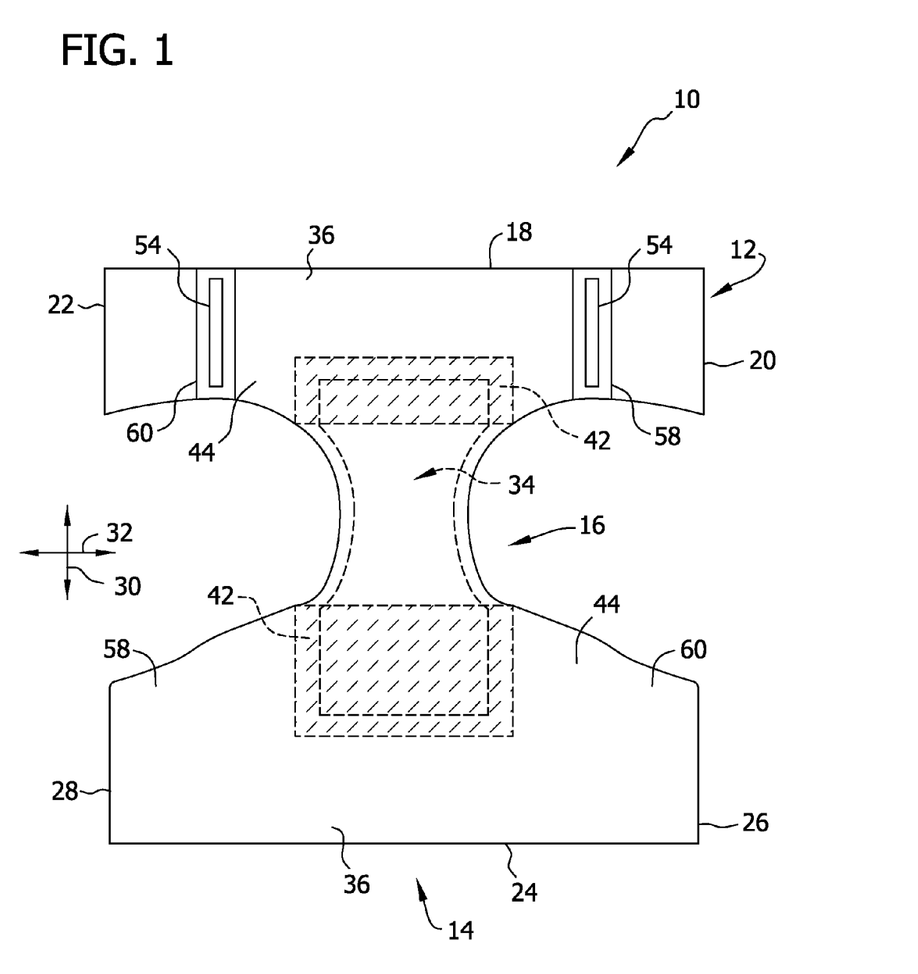
FIG. 1 is a plan view of one embodiment of an absorbent article, the article being in a longitudinally stretched and laid-flat condition showing a surface of the article that faces the wearer during wear.
Figure 2:
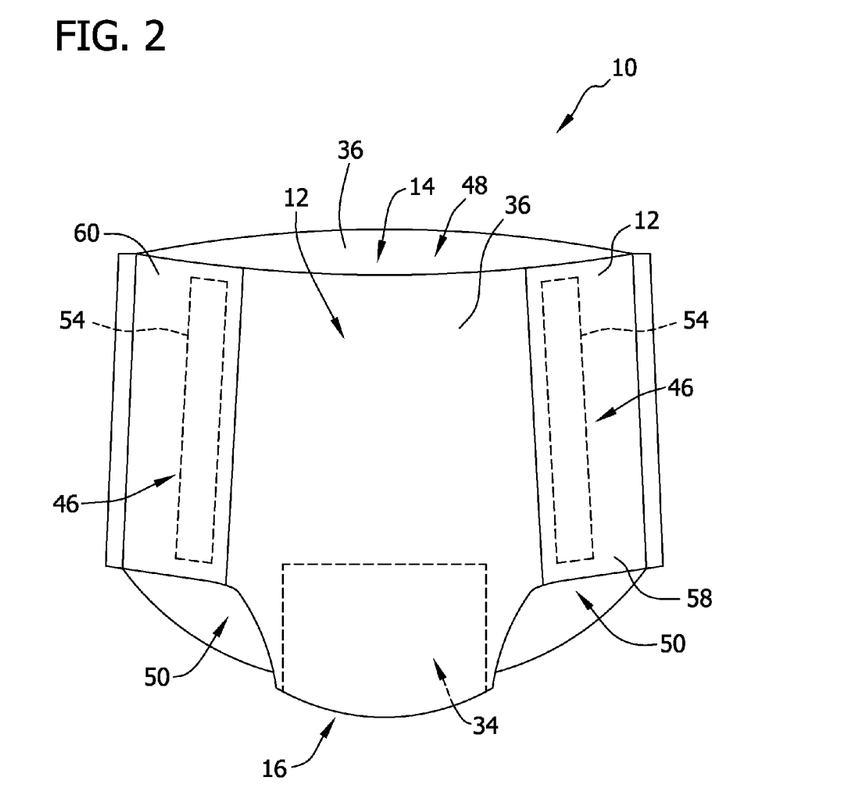
FIG. 2 is a front view of the absorbent article of FIG. 1 with front and back waist regions of the article joined by a fastening assembly such that the garment is in a pull-on, pant-like configuration.

FIGS. 1 and 2 illustrate one suitable embodiment of an absorbent article, indicated generally at 10. The absorbent article 10 has a front region 12, a back region 14, and a crotch region 16 disposed longitudinally between and interconnecting the front and back regions. The front, back and crotch regions 12, 14, 16 are indicated generally by the respective reference number. In the front region 12, the absorbent article 10 has a front edge 18 and transversely opposed first and second front side edges 20, 22. A back edge 24 and transversely opposed first and second back side edges 26, 28 are located in the back region 14 of the absorbent article 10. As illustrated in FIG. 1, the absorbent article 10 defines a longitudinal direction 30 and a transverse direction 32, which is perpendicular to the longitudinal direction.

The absorbent article 10 includes an absorbent insert, indicated generally at 34, that extends longitudinally from the front region 12 through the crotch region 16 to the back region 14. The absorbent member 34 can be constructed of materials suitable for absorbing liquid excretions, such as wood pulp fluff, superabsorbent polymers, absorbent foam, and the like. The absorbent member 34 can be encased in one or more substrates. For example, the absorbent member 34 can be wrapped in a tissue and/or a nonwoven substrate.

The front and back regions 12, 14 of the illustrated absorbent article 10 are constructed of discrete pieces of laminate 36 that are connected via the absorbent insert 34. That is, the front region 12 is formed by a piece of laminate 36 and the back region 14 is formed by a separate piece of laminate. In one embodiment, front region 12 and back region 14 are formed by a single piece of laminate. As seen in FIG. 1, the laminate 36 forming the front region 12 is spaced from the laminate forming the back region 14 to define a gap G. The absorbent insert 34 spans the gap G and connects the laminate 36 forming the front region 12 to the laminate forming the back region 14.

In one suitable embodiment, the laminate 36 used to form both the front and back regions 12, 14 of the absorbent article 10 comprises a polymeric film layer and at least one nonwoven layer. In the illustrated embodiment, for example, the laminate 36 has two nonwoven layers superposed on opposing top and bottom surfaces of the polymeric film such that the polymeric film is sandwiched between the two nonwoven layers. The polymeric film and both nonwoven layers extend substantially throughout the entire area of the laminate 36. While the laminate 36 used to form the front and back regions 12, 14 is the same in the illustrated absorbent article 10, it is contemplated that the laminate used to form the front region 12 can be different than the laminate used to form the back region 14.

As seen in FIG. 1, a portion of the absorbent insert 34 overlaps a portion of the laminate 36 in the front and back regions 12, 14 to define overlapped regions 42 and non-overlapped regions 44. In one suitable embodiment, at least a portion of each of the overlapped regions 42 of the laminate 36 is non-elastomeric, and at least a portion of the non-overlapped region 44 of the laminate 36 is elastomeric. The overlapped regions 42 are indicated in FIG. 1 by a pattern of diagonally extending dashes.

In one suitable embodiment, the entire laminate 36 forming the front and back regions 12, 14 is constructed of an elastomeric film laminate having portions (e.g., the portions generally corresponding to the overlapped regions 42) thereof "deactivated" or "deadened" to render it non-elastomeric. As used herein, "elastomeric" refers to a material or composite that can be elongated by at least 50 percent of its relaxed length and that will recover, upon release of the applied force, at least 50 percent of its elongation. It is generally preferred that the elastomeric material or composite be capable of being elongated by at least 100 percent, more preferably by at least 200 percent, of its relaxed length and recover, upon release of an applied force, at least 50 percent of its elongation. "Non-elastomeric" refers to a material or composite that is non-extensible, or that is extensible but will recover no more than 20 percent of its elongated length after release of an applied elongating force. "Non-extensible" refers to a material that cannot stretch or extend by more than 25 percent of its relaxed length without fracture upon application of a biasing force. "Partially elastomeric" refers to a material or composite which can be elongated by at least 50 percent of its relaxed length and which will recover, upon release of the applied force, more than 20 percent but less than 50 percent of its elongation.

It should be noted that in analyzing the laminate 36 or regions thereof for extensible or elastic character, the laminate is to be examined with the laminate 36 removed from separately attached components. For example, before examining the extensible or elastic properties of the overlapped regions 42 of the laminate 36, the absorbent insert 34 should be removed. That is, the absorbent insert 34 should be peeled away from the laminate 36 prior to examining extensibility or elasticity of any portion of the laminates.

In one suitable embodiment, the majority of the overlapped region 42 of each of the laminates 36 is non-elastomeric. That is, more than 50 percent of the area of the overlapped region 42 of the laminates 36 is non-elastomeric. In one suitable embodiment, more than 75 percent, and in still a more suitable embodiment more than 90 percent of the area of the overlapped region 42 of the laminates 36 is non-elastomeric. In another suitable embodiment, the entire overlapped region 42 of the laminates 36 (i.e., 100 percent) is non-elastomeric. For example, in the absorbent article 10 illustrated in FIG. 1, the entire overlapped region 42 of the laminates 36 is non-elastomeric and generally the same size and shape as the portion of the absorbent insert 34 that overlaps it.

In other suitable embodiments, the portion of the laminates 36 rendered non-elastomeric can be larger than the corresponding overlapped region 42. For example, the non-elastomeric area of the laminates 36 can be 125 percent or less larger, more preferably 120 percent or less larger, and still more preferably 110 percent or less larger in area than the overlapped region 42. By having the non-elastomeric region of the laminates 36 larger than the area of the overlapped regions 42, it is possible to accommodate the process registration variability common in typical high-speed absorbent article manufacturing processes. In other words, the footprint of the non-elastomeric region of the laminates 36 being larger relative to the footprint of the absorbent insert 34 in the front and back regions 12, 14 of the absorbent article 10 allows for variability in registration as the absorbent insert is mated to the laminates. Furthermore, in such embodiments, the relatively larger non-elastomeric region (larger relative to the overlapped region 42) will aid in minimizing the amount of bunching directly around the periphery of the absorbent insert 34, which can provide a smoother, "flatter", more underwear-like garment.

Figure 3:
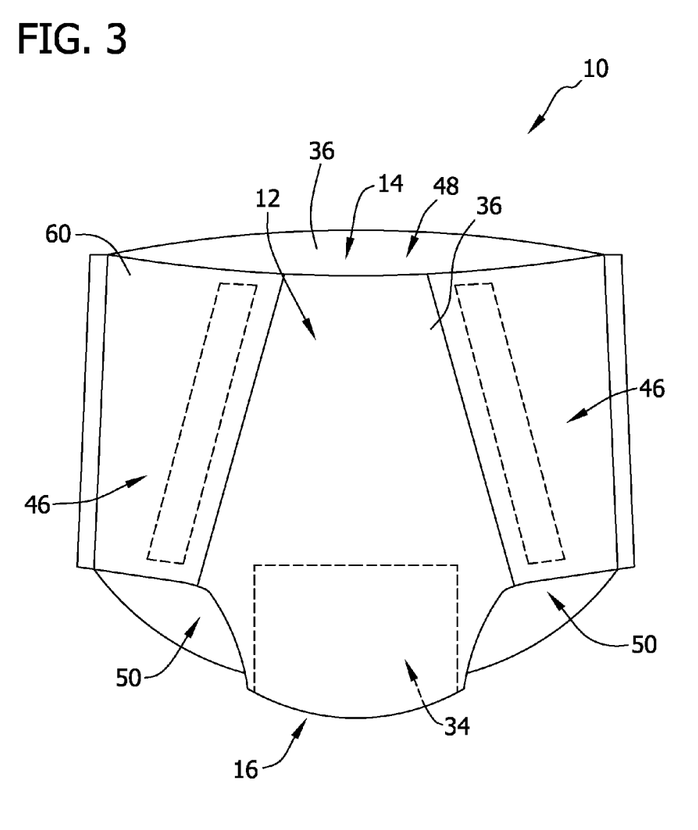
FIG. 3 is another front view of the absorbent article of FIG. 1 with another embodiment of a fastening assembly.

As seen in FIGS. 2 and 3, the absorbent article 10 includes a fastening assembly, indicated generally at 46, that facilitates attaching the back region 14 to the front region 12 to define a pull-on, pant-like configuration of the absorbent article 10 having a waist opening, indicated at 48, and two leg openings, indicated at 50. The fastening assembly 46 includes a pair of fastening members 54 that are attached to the front region 12. The pair of fastening members 54 is attached to the front region 12 such that the absorbent article 10 includes a left-handed fastening member attached to a first discrete part 58 of the front region 12, and a right-handed fastening member attached to a second discrete part 60 of the front region 12. As seen in FIGS. 2 and 3, the first and second discrete parts 58, 60 of the front region 12 are configured to overlap with a portion of the back region 14.

With reference again to FIGS. 2 and 3, each of the fastening members 54 is adapted to releasably attach to the back region 14 to thereby join the front region 12 and the back region 14 together. Thus, the absorbent article 10 can be selectively moved between an opened configuration wherein the fastening members 54 disposed on the first and second discrete parts 58, 60 are disengaged (i.e., not attached) to the back region 14, and a closed configuration wherein the fastening members 54 are engaged (i.e., attached) to the back region 14. The absorbent article 10 is illustrated in its closed configuration in FIGS. 2 and 3. As illustrated in FIG. 3, the fastening members 54 can be angled.

Figure 4:
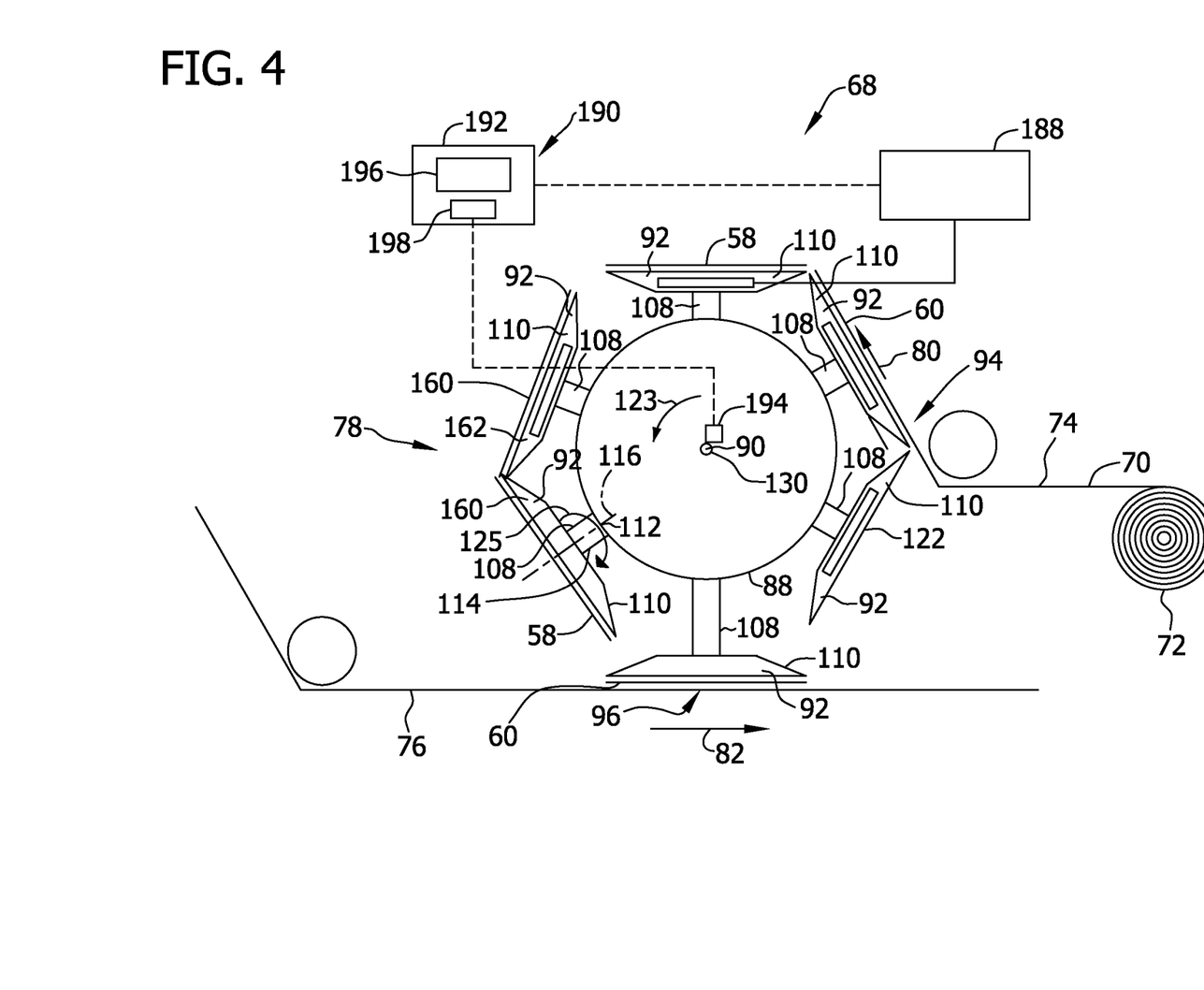
FIG. 4 illustrates one embodiment of a manufacturing process for manufacturing the absorbent article illustrated in FIGS. 1-3.
Figure 5:
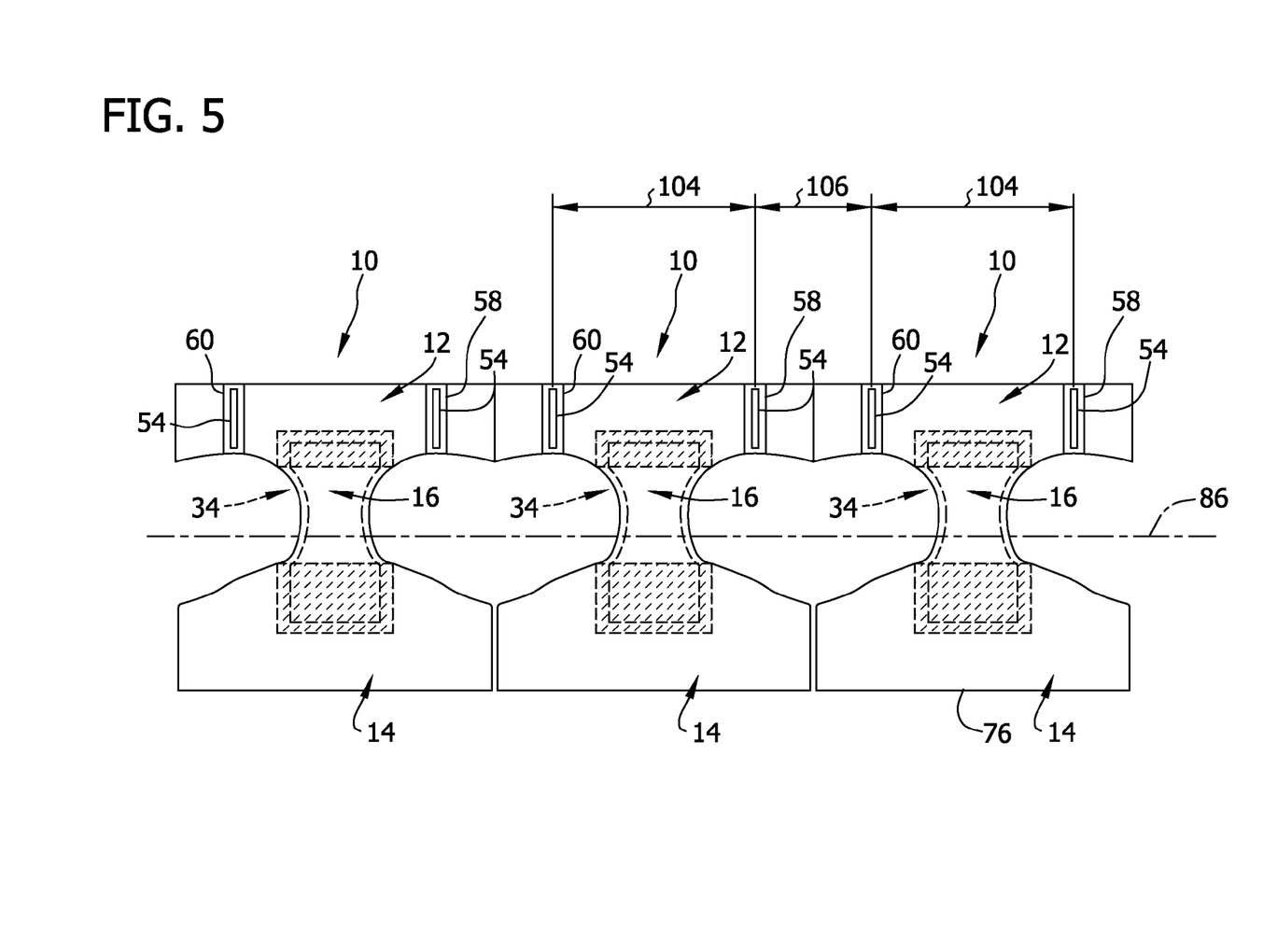
FIG. 5 is a top view of a substrate web manufactured with the manufacturing process illustrated in FIG. 4 for manufacturing the absorbent article illustrated in FIGS. 1-3.

FIG. 4 schematically illustrates a portion of one embodiment of a process 68 suitable for making a plurality of absorbent articles 10 illustrated in FIGS. 1-3. As seen in FIG. 4, a supply of web 70 used to form the first and second discrete parts 58, 60 of the absorbent article 10 are provided from suitable supply sources (e.g., supply roll 72).

The web 70 is fed to a web treatment apparatus, indicated generally at 78, to assemble at least a portion of the absorbent article 10. More specifically, the treatment apparatus 78 receives the web 70 as it is traveling in a first direction, represented by arrow 80. In one suitable embodiment, the web 70 includes a plurality of discrete parts 58, 60 separated by a plurality of preformed perforations or other suitable lines of weakness. It is contemplated, however, that a plurality of separated first and second discrete parts 58, 60 can be fed to the treatment apparatus 78. It is also contemplated that the web 70 can be cut into a plurality of first and second discrete parts 58, 60 after the web is fed to the treatment apparatus 78.

In one embodiment, the treatment apparatus 78 includes a drive assembly 88 configured to rotate about a drive axis 90, and a plurality of transfer segments 92 that are coupled to and extend outwardly from the drive assembly. The drive assembly 88 includes one or more drive sources including, for example, servo motors, and/or camboxes, that are coupled to each transfer segment 92. The drive assembly 88 is configured to rotate each transfer segment 92 about the drive axis 90 between a pick-up location, indicated generally at 94, and an application location, indicated generally at 96.

As illustrated in FIG. 4, the transfer segment 92 is configured to receive the web 70 comprising the plurality of first and second discrete parts 58, 60 at the pick-up location 94, and convey the discrete parts 58, 60 to the application location 96. In the illustrated configuration, each of the discrete parts 58, 60 is separated from an adjacent discrete part along the preformed perforation (or other line of weakness) as the web 70 is conveyed by the treatment apparatus 78. More specifically, and as described below in more detail, each of the discrete parts 58, 60 is received by one of the transfer segments 92. During rotation by the drive assembly 88, each of the adjacent transfer segments 92 of the treatment apparatus 78 moves apart thereby causing the web 70 of discrete parts 58, 60 to rupture about the preformed perforations. Thus, each of the transfer segments 92 is adapted to carry one of the discrete parts 58, 60 (i.e., either one of the first discrete parts or one of the second discrete parts).

In a suitable embodiment, the web treatment apparatus 78 is an oscillating cam adjusted roller as is disclosed in U.S. Pat. Nos. 5,716,478, 5,759,340, and 6,139,004, all of which are assigned to Kimberly-Clark Worldwide, Inc., and the entire disclosures of all of which are hereby incorporated herein by reference.

With reference still to FIG. 4, each of the transfer segments 92 includes a support arm 108 extending radially outwardly from the drive assembly 88, and a transfer puck 110 rotatably coupled to the support arm 108. The support arm 108 includes a first end 112, which is coupled to the drive assembly 88, and an opposite second end 114, which is coupled to the transfer puck 110. The support arm 108 extends between the first end 112 and the second end 114 along a radial axis 116. In one suitable embodiment, the first end 112 of the support arm 108 is coupled to the drive assembly 88 such that each transfer puck 110 is independently rotatable about both the drive axis 90 of the treatment apparatus 78 (as indicated by arrow 123 of FIG. 4) and the radial axis 116 (as indicated by arrow 125 of FIG. 4).

Figure 6:
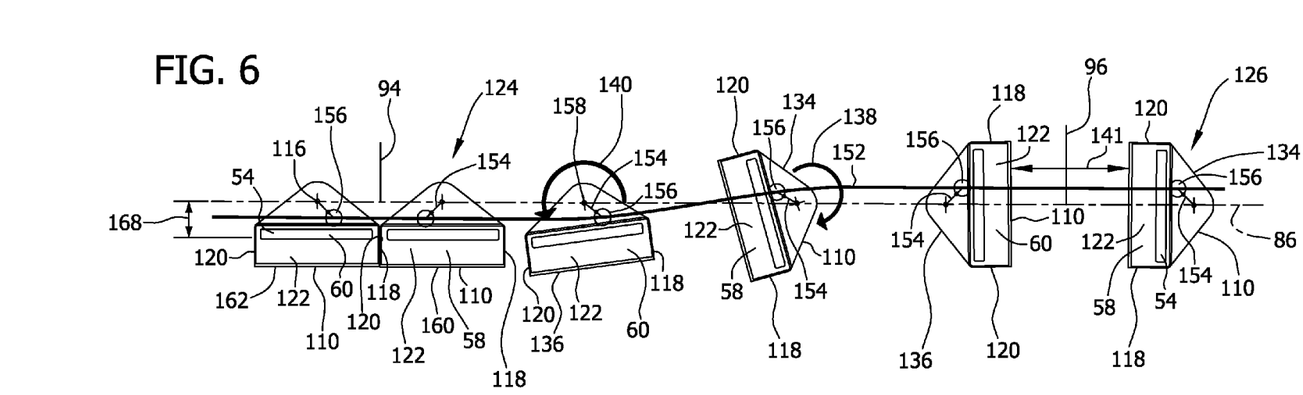
FIGS. 6-8 illustrate a portion of the manufacturing process illustrated in FIG. 4.

As illustrated in FIG. 6, each transfer puck 110 includes a leading edge 118, a trailing edge 120, and a platform 122 that extends between the leading edge and the trailing edge. The platform 122 of each of the transfer pucks is sized and shaped to receive one of the first and second discrete parts 58, 60 from the web 70, and release the discrete parts 58, 60 to apply the discrete parts 58, 60 to the second substrate web 76.

As mentioned above, the transfer puck 110 is pivotable about the support arm axis 116. More specifically, the transfer puck 110 is pivotable between a first position, indicated generally at 124 in FIG. 6, wherein the transfer puck is oriented to receive one of the first and second discrete parts 58, 60 at the pick-up location 94 and a second position, indicated generally at 126 in FIG. 6, wherein the transfer puck 110 is oriented to apply respective one of the first and second discrete parts 58, 60 to a substrate 76 at the application location 96.

In one suitable embodiment, the web 70 of discrete parts 58, 60 is traveling at a first speed in the first direction 80, and the substrate 76 is traveling at a second speed in a second direction 82 that is different than the first speed. The drive assembly 88 is adapted to rotate each transfer segment 92 about the drive axis 90 such that the surface speed of each transfer puck 110 is approximately equal to the speed of the web 70 as the first and second discrete parts 58, 60 are received by the platforms 122 of the transfer pucks 110 at the pick-up location 94. In the illustrated embodiment, the drive assembly 88 accelerates each transfer segment 92 such that the speed of the transfer puck 110 is approximately equal to the speed of the substrate 76 as the discrete parts 58, 60 are applied to the substrate 76 by the transfer pucks at the application location 96.

In one embodiment, each of the transfer pucks 110 is rotated about a puck axis 130. The drive assembly 88 rotates each transfer puck 110 about puck axis 130 between the pick-up location 94 and the application location 96. In one suitable embodiment, the drive assembly 88 is configured to selectively adjust a rotational speed of each transfer puck 110, as each transfer puck 110 is rotated between the pick-up location 94 and the application location 96. More specifically, the drive assembly 88 selectively rotates each transfer puck 110 at a first rotational speed from the pick-up location 94 to the application location 96, and rotates each transfer puck 110 a second rotational speed from the application location 96 to the pick-up location 94 that is different than the first rotational speed. In addition, drive assembly 88 may selectively rotate each transfer puck 110 at a different rotational speed between the pick-up location 94 and the application location 96 to enable the treatment apparatus 96 to apply each discrete part 58, 60 at a variable spacing along a placement axis 86.

Figure 7:
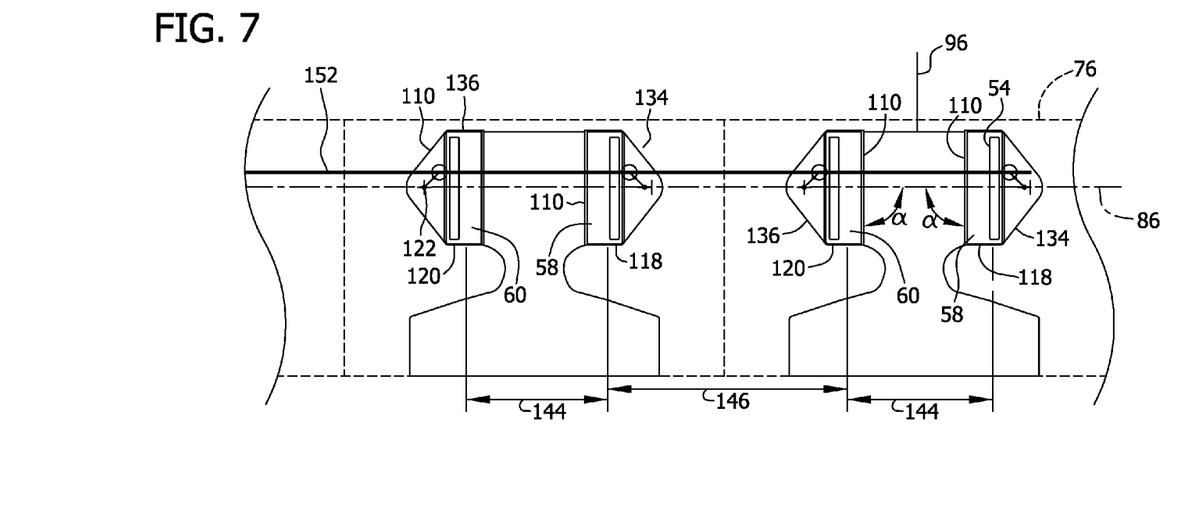
Figure 8:
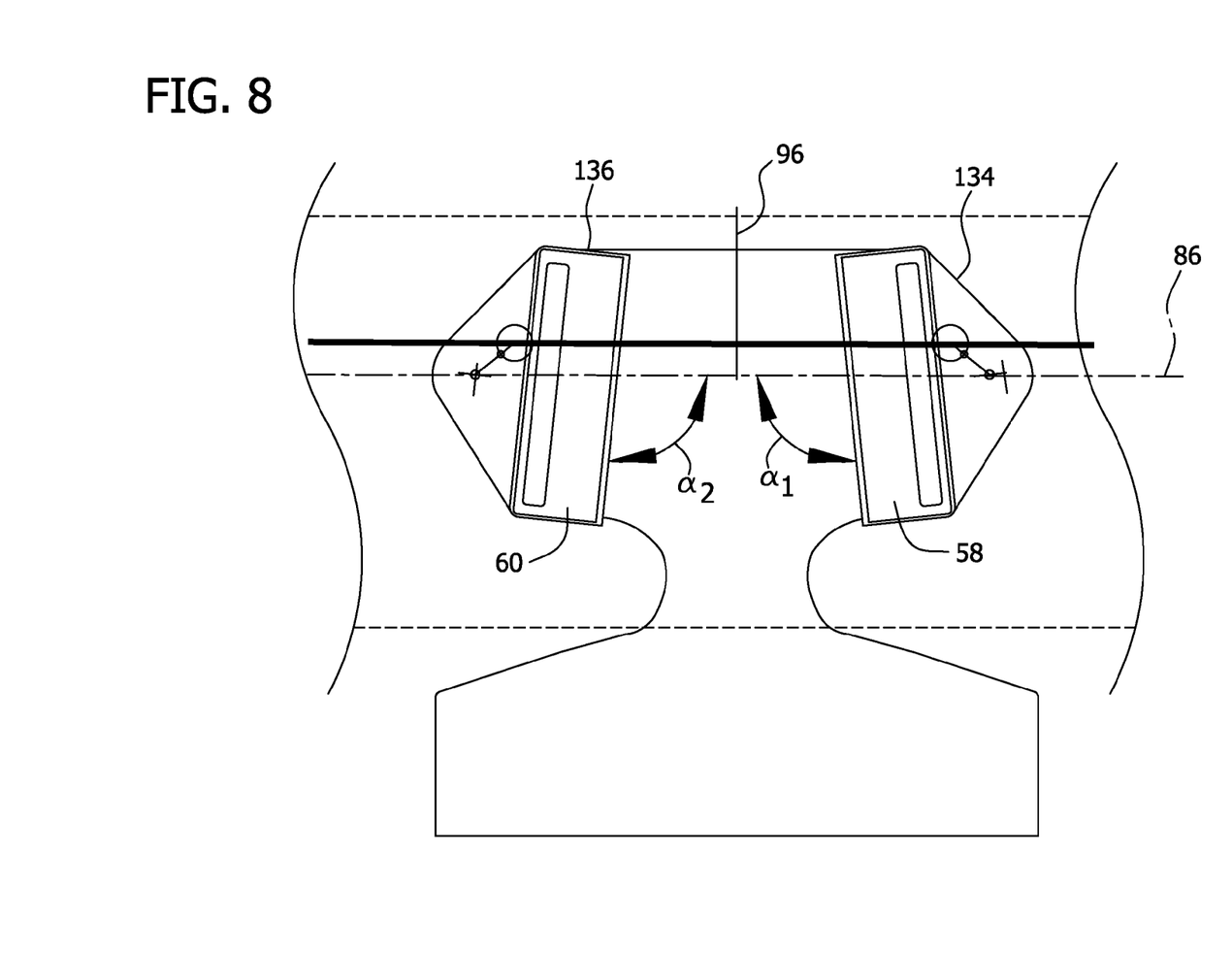

In one suitable embodiment, the apparatus 78 can be used to apply alternating first and second discrete pieces 58, 60 to a continuously moving product web including at least one portion of the absorbent article 10 (e.g., a continuous web of laminate 36 used to form the back region 14 of the absorbent article). It is contemplated that other portions of the absorbent article 10 can be applied to the continuous web of laminate 36 including, for example, the absorbent insert 34 and the laminate 36 forming the front waist region 12 of the absorbent article (as illustrated in FIGS. 6-8). Each transfer puck 110 is configured to receive either one first discrete part 58 or one second discrete part 60 and apply the respective discrete part in its proper location in the back waist region 14 of the absorbent article 10.

FIGS. 6 and 8 are schematic expanded circumferential views of a path of travel of web treatment apparatus 78 illustrating the relative positioning of adjacent transfer pucks 110 as they travel from the pick-up location 94 to the application location 96. The pair of transfer pucks includes a first (or leading) transfer puck 134, and an adjacent second (or trailing) transfer puck 136. The drive assembly 88 is configured to pivot the first transfer puck 134 about the support arm axis 116 in a first rotation direction, represented by arrow 138 in FIG. 6, such as, for example, a clockwise direction, and to pivot the second transfer puck 136 in a second rotational direction, represented by arrow 140 in FIG. 6, that is opposite the first rotation direction such as, for example, a counterclockwise direction.

It is also contemplated that the drive assembly 88 can be configured to properly space the first and second transfer pucks 134, 136 relative to each other such that the first transfer puck is properly spaced relative to the second transfer pucks at the application location 96. That is, the drive assembly 88 can be configured such that the distance (or spacing) 141 between the first and second transfer pucks 134, 136 can be adjusted as the drive assembly rotates the first and second transfer pucks 134, 136 about the drive axis 90.

FIG. 7 illustrate the relative position of two adjacent pairs of transfer pucks 110 with respect to the second substrate web 76. In one embodiment, the web treatment apparatus 78 and more specifically the drive assembly 88 orients each of the pairs of transfer pucks 110 relative to each other such that each of the transfer pucks 110 are generally aligned along the placement axis 86. In the illustrated embodiment, the drive assembly 88 rotates the first and second transfer pucks 134, 136 of each pair of transfer pucks 110 about the corresponding support arm axis 116 such that a center portion of the second transfer puck 136 is spaced a first circumferential distance 144 along the placement axis 86 from the center portion of the first transfer puck 134, and the center portion of the first transfer puck 134 of the adjacent transfer puck pair is spaced a second circumferential distance 146 from the second transfer puck 136 along the placement axis 86 that is different than the first circumferential distance, as is illustrated in FIG. 7. In the illustrated embodiment, the second circumferential distance 146 is less than the first circumferential distance 144. It is contemplated that, in other embodiments, the second circumferential distance 146 can be greater than the first circumferential distance 144.

Moreover, in a suitable embodiment, the first transfer puck 134 of each pair of transfer pucks 110 conveys the first discrete part 58, and the second transfer puck 136 conveys the second discrete part 60. The first transfer puck 134 is rotated in the first direction 138, and the second transfer puck 136 is rotated in the second direction 140 such that the first discrete part 58 is spaced the first distance 104 from the second discrete part. The second discrete part 60 is spaced the second distance 106 from the first discrete part 58 of the trailing pair of discrete parts.

In the embodiment illustrated in FIG. 7, each of the first and second transfer pucks 134, 136 is rotated such that the first and second discrete parts 58, 60 are applied to the substrate 76 at an angle α with respect to the placement axis 86, which is approximately equal to 90°. In another embodiment, which is illustrated in FIG. 8, each of the first and second transfer pucks 134, 136 is rotated at different angles with respect to the placement axis 86 such that the first discrete part 58 is applied at a first angle $\alpha_1$ and the second discrete part 60 is applied at a second angle $\alpha_2$ that is different than the first angle $\alpha_1$. In one suitable embodiment, the second discrete part 60 is applied at the second angle $\alpha_2$ that is equal to, and opposite from, the first angle $\alpha_1$. By applying the first and second discrete parts 58, 60 at opposing, angled orientations, the apparatus 78 can manufacture the absorbent article 10 of FIG. 3.

In one suitable embodiment illustrated in FIGS. 6 and 7, the drive assembly 88 includes a cylinder cam coupled to each transfer segment 92 to rotate the respective transfer puck 110 about the support arm axis 116. The cylinder cam includes a radial outer surface and a cam track 152 defined along the radial outer surface (FIG. 6). As illustrated in FIG. 6, each transfer segment 92 includes a cam arm 154, and a cam follower 156 coupled to the cam arm. The cam arm 154 is coupled to the transfer puck 110, and to a pivot point 158. The cam follower 156 is adapted to engage the cam track 152 to facilitate selectively pivoting the transfer puck 110 about the pivot point 158.

In one embodiment, the apparatus 78 includes a first transfer segment 160 associated with the first transfer puck 134 and an adjacent second transfer segment 162 associated with the second transfer puck 136. The cam follower 156 of the first transfer segment 160, which is a trailing cam follower, is positioned nearer the puck's trailing edge 120 than the puck's leading edge 118. The cam follower 156 of the second transfer segment 162, which is a leading cam follower, is positioned nearer to the puck's leading edge 118 than the puck's trailing edge 120. In addition, in one embodiment, the platforms 122 of the transfer pucks 110 are offset a distance 168 from the pivot point 158 to enable the transfer puck 110 to receive the first and second discrete parts 58, 60 such that the discrete parts are offset from the pivot point 158.

Figure 9:
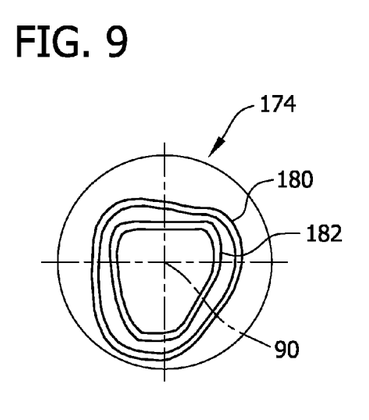
FIGS. 9-11 are schematic views of a portion of a drive assembly that may be used with the manufacturing process illustrated in FIG. 4.
Figure 10:
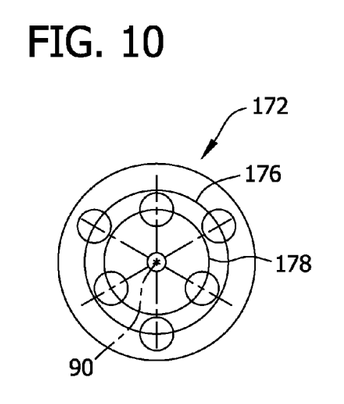
Figure 11:
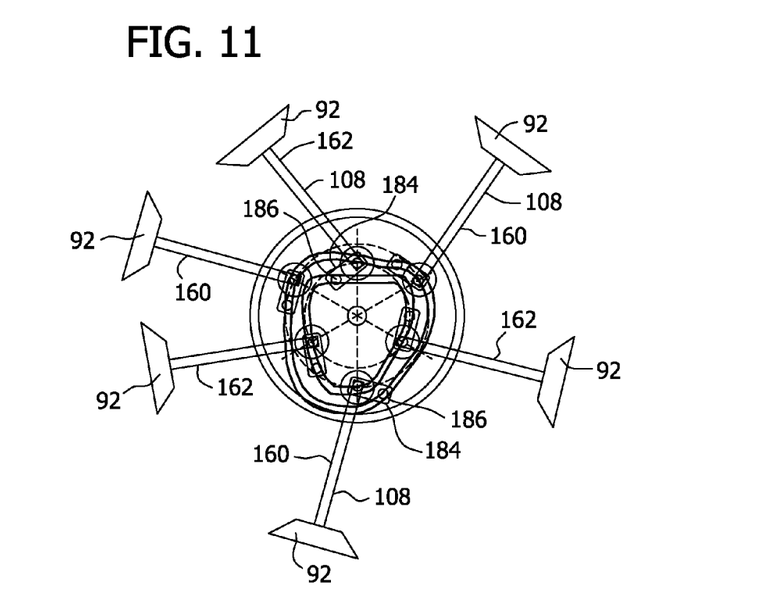

FIGS. 9-11 are schematic views of a portion of one suitable embodiment of the drive assembly 88. As mentioned above, the web apparatus 78 includes a plurality of pairs of transfer pucks 110 with each pair comprising a first transfer puck 134 and a second transfer puck 136. The illustrated drive assembly 88 is configured to rotate (and space if necessary) each pair of transfer pucks 110 such that the first transfer puck 134 is spaced the first circumferential distance 144 (shown in FIG. 7) from the second transfer puck 136 at the application location 96. In addition, the drive assembly 88 is configured to rotate (and space if necessary) the pairs of transfer pucks 110 such that the second transfer puck 136 of a leading pair of transfer pucks is spaced from the first transfer puck 134 of a trailing pair of transfer pucks the second circumferential distance 146 (shown in FIG. 7) at the application location 96.

As seen in FIGS. 9 and 10, the drive assembly 88 includes a drive ring assembly 172 and a cam plate assembly 174. The drive ring assembly 172 and cam plate assembly 174 are each coupled to each transfer segment 92 to rotate the transfer segments about the drive axis 90. The drive ring assembly 172 includes a first drive ring 176 and a second drive ring 178 that is coaxially aligned with the first drive ring 176. In one embodiment, the first drive ring 176 is rotated at a first rotational speed, and the second drive ring 178 is rotated at a second rotational speed that is approximately equal to the first rotational speed. Alternatively, the first rotational speed may be different than the second rotational speed.

As illustrated in FIG. 9, the cam plate assembly 174 includes a first cam track 180, and a second cam track 182 that is coaxially aligned with the first cam track 180. In one embodiment, the cam plate assembly 174 includes a cam plate that includes first cam track 180 and second cam track 182. In another embodiment, the cam plate assembly 174 includes a plurality of cam plates that each includes one or more cam tracks. With reference now to FIG. 11, each transfer segment 92 includes a cam arm 184 and a cam follower 186. The cam arm 184 is pivotably coupled to the support arm 108. The support arm 108 and/or the cam arm 184 are in turn coupled to the drive assembly 88. The cam follower 186 is coupled to the cam arm 184 and is adapted to engage one of the cam tracks 180, 182.

In one embodiment, the first drive ring 176 is coupled to a first transfer segment 160 of the plurality of transfer segment pairs, and the second drive ring 178 is coupled to a second transfer segment 162 of the plurality of transfer segment pairs. In addition, each first transfer segment 160 is adapted to engage the first cam track 180, and each second transfer segment 162 is adapted to engage the second cam track 182. Moreover, in another embodiment, each second transfer segment 162 is positioned between adjacent first transfer segments 160 such that adjacent transfer segments 92 alternatively engage the first and second cam tracks 180 and 182, respectively.

Referring to again to FIG. 4, in a suitable embodiment, the apparatus 78 includes a vacuum assembly 188 that is coupled to each transfer puck 110 to selectively apply a vacuum suction through the platform 122 to enable the transfer puck 110 to selectively receive, hold and release the respective discrete parts 58, 60.

A control system 190 is coupled in operative control communication with the drive assembly 88 and with vacuum assembly 188 to operate the drive assembly 88 and the vacuum assembly 188 to convey first and second discrete parts 58, 60 from the web 74, and to apply the discrete parts 58, 60 to the substrate 76. The control system 190 includes a controller 192 that is coupled to the drive assembly 88, the vacuum assembly 188, and one or more sensors 194. Each sensor 194 senses various parameters relative to the operation of the drive assembly 88, the transfer segments 92, and/or the vacuum assembly 188. The sensors 194 may include, but are not limited to only including, position sensors, angular speed sensors, proximity sensors, and/or any other sensors that sense various parameters relative to the operation of the apparatus 78. The sensors 194 can be any suitable sensors such as, for example, encoders, reed switches, reed sensors, infra-red type sensors, and/or photo-eye sensors. Alternatively, any sensors that enable operation of the apparatus 78, as described herein may be used.

In one embodiment, the controller 192 includes a processor 196 and a memory device 198. The processor 196 includes any suitable programmable circuit which may include one or more systems and microcontrollers, microprocessors, reduced instruction set circuits (RISC), application specific integrated circuits (ASIC), programmable logic circuits (PLC), field programmable gate arrays (FPGA), and any other circuit capable of executing the functions described herein. The above examples are exemplary only, and thus are not intended to limit in any way the definition and/or meaning of the term "processor." Memory device 198 includes a computer readable medium, such as, without limitation, random access memory (RAM), flash memory, a hard disk drive, a solid state drive, a diskette, a flash drive, a compact disc, a digital video disc, and/or any suitable device that enables processor 196 to store, retrieve, and/or execute instructions and/or data.

In one embodiment, the control system 190 is configured to sense a position of each transfer puck 110 with respect to the first substrate web 74, and energize the vacuum assembly 188 when the transfer puck 110 is at the pick-up location 94 adjacent the web 70 to cause the discrete part 58, 60 to adhere to the platform 122 of the transfer puck. In addition, the control system 190 senses a position of each transfer puck 110 with respect to the substrate 76, and de-energizes the vacuum assembly 188 to release the respective discrete part 58, 60 from the platform 122 of the transfer puck to enable the transfer puck to release and thereby apply the discrete part to the substrate 76.

Figure 12:
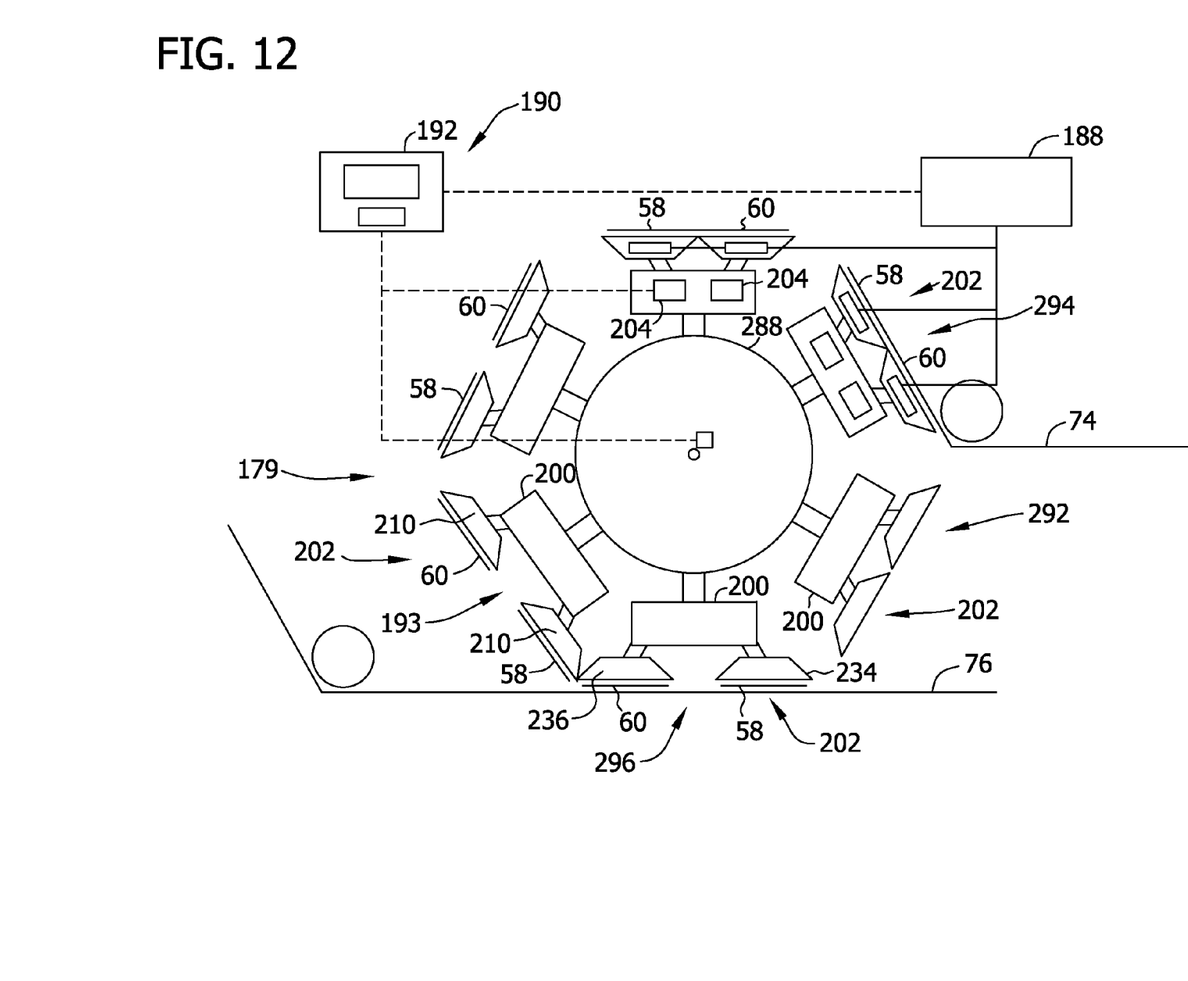
FIG. 12 illustrates another embodiment of a manufacturing process for manufacturing the absorbent article illustrated in FIGS. 1-3.

FIG. 12 illustrates another embodiment of a web treatment apparatus, indicated generally at 179. In one suitable embodiment, the apparatus comprises a plurality of transfer segment 193 including a base transfer member 200, and a pair 202 of transfer pucks 110. The base transfer member 200 is coupled to a drive assembly 288. The transfer puck pair 202 is coupled to the base transfer member 200. The transfer puck pair 202 is adapted to convey a corresponding pair of discrete parts 58, 60 from a pick-up location 294 to an application location 296. The drive assembly 288 is configured to rotate each base transfer member 200 such that adjacent pairs 202 of transfer pucks 210 are spaced the second circumferential distance 146 (shown in FIG. 7) at the application location 296.

In addition, the transfer puck pair 202 includes a first transfer puck 234 and a second transfer puck 236. As the drive assembly 288 rotates the transfer segment 292 from the web 74 towards the substrate 76, the drive assembly 288 moves the second transfer puck 236 away from the first transfer puck 234 along the circumferential path of travel such that the second transfer puck is spaced the first circumferential distance 144 (shown in FIG. 7) from the first transfer puck. In one embodiment, the drive assembly 288 moves each of the first and second transfer pucks 234 and 236 away from each other. Alternatively, the drive assembly 288 may be configured to move the first transfer puck 234, or the second transfer puck 236, respectively.

In one suitable embodiment, the drive assembly 288 includes a plurality of servomechanisms 204 that are coupled to each first and second transfer puck 234 and 236. The control system 190 is coupled to each servomechanism 204 to selectively move the first transfer puck 234 and/or the second transfer puck 236 away from the corresponding transfer puck 210 along the circumferential path of travel.

When introducing elements of the present invention or the preferred embodiment(s) thereof, the articles "a", "an", "the", and "said" are intended to mean that there are one or more of the elements. The terms "comprising," "including", and "having" are intended to be inclusive and mean that there may be additional elements other than the listed elements.

As various changes could be made in the above constructions without departing from the scope of the invention, it is intended that all matter contained in the above description or shown in the accompanying drawings shall be interpreted as illustrative and not in a limiting sense.

What is claimed is:

1. Apparatus for conveying a plurality of discrete parts and applying each discrete part to a substrate moving along a placement axis of the apparatus, the apparatus comprising:
   a plurality of transfer pucks adapted to convey the discrete parts to the substrate, the plurality of transfer pucks comprising a first transfer puck and a second transfer puck; and
   a drive assembly configured to rotate the first transfer puck in a first rotational direction and to rotate the second transfer puck in a second rotational direction that is opposite the first rotational direction such that a plurality of pairs of discrete parts is applied to the substrate and perpendicular to the placement axis, wherein each applied pair of discrete parts includes a first discrete part and a second discrete part spaced a first distance along the placement axis from the first discrete part, adjacent pairs of discrete parts being spaced a second distance along the placement axis that is different from the first distance.

2. The apparatus as set forth in claim 1, further comprising a plurality of transfer segments, each of the transfer segments comprising a support arm extending outwardly from the drive assembly, and one of the plurality of transfer pucks coupled to the support arm and configured to pivot about the support arm, each of the transfer pucks being pivotable between a first position wherein the transfer puck is oriented to receive one of the first and second discrete parts, and a second position wherein the transfer puck is oriented to apply the one of the first and second discrete parts to the substrate.

3. The apparatus as set forth in claim 2, wherein the drive assembly being configured to pivot the first transfer puck about the support arm axis in the first rotational direction, and to pivot the second transfer puck in the second rotational direction that is opposite the first rotational direction.

4. The apparatus as set forth in claim 3, wherein the drive assembly rotates the first and second transfer pucks such that the first discrete part is applied at a first angle with respect to a placement axis, and the second discrete part is applied at a second angle with respect to the placement axis, wherein the first angle is different than the second angle.

5. The apparatus as set forth in claim 2, wherein the drive assembly comprises a cylinder cam, each transfer segment of the plurality of transfer segments comprises:
a cam arm extending outwardly from the support arm; and
a cam follower adapted to engage the cylinder cam to selectively pivot the transfer segment about the support arm.

6. The apparatus as set forth in claim 5, wherein the plurality of transfer segments comprise a first transfer segment having a leading cam follower, and a second transfer segment having a trailing cam follower.

7. The apparatus as set forth in claim 2, wherein each of the transfer pucks comprises a platform adapted to contact the first and second discrete parts to convey the discrete parts to the substrate, each of the transfer pucks being coupled to the support arm at a pivot point such that the outer surface is offset a distance from the pivot point.

8. The apparatus as set forth in claim 2, further comprising a vacuum assembly coupled to each transfer puck, the vacuum assembly configured to selectively apply a vacuum to each transfer puck to facilitate conveying each discrete part to the substrate.

9. The apparatus as set forth in claim 1, wherein the drive assembly selectively adjusts a rotational speed of the plurality of transfer pucks as each transfer puck of the plurality of transfer pucks rotates between a pick-up location and an application location.

10. The apparatus as set forth in claim 9, wherein the drive assembly selectively rotates each transfer puck of the plurality of transfer pucks at a first rotational speed from the pick-up location to the application location, and rotates each transfer puck of the plurality of transfer pucks at a second rotational speed from the application location to the pick-up location that is different than the first rotational speed.

11. The apparatus as set forth in claim 1, wherein the drive assembly selectively adjusts a distance between the first transfer puck and the second transfer puck as the drive assembly rotates the first transfer puck and the second transfer puck.

12. The apparatus as set forth in claim 1, wherein the drive assembly orients a pair of transfer pucks of the plurality of transfer pucks relative to each other such that the pair of transfer pucks is aligned along the placement axis of the substrate.

13. A method of applying a plurality of discrete parts to a substrate moving along a placement axis comprising:
directing a web including the plurality of discrete parts toward an apparatus for conveying each discrete part from the web and applying each discrete part to the substrate, the apparatus including a plurality of transfer pucks rotatably coupled to a drive assembly;
rotating a first transfer puck of the plurality of transfer pucks in a first direction;
rotating a second transfer puck of the plurality of transfer pucks in a second direction that is different than the first direction such that each discrete part from the web is conveyed to the substrate,
applying a plurality of pairs of discrete parts including a first discrete part and a second discrete part to the substrate and perpendicular to the placement axis such that the applied second discrete part is spaced a first distance along the placement axis from the applied first discrete part, and adjacent applied pairs of discrete parts being spaced a second distance along the placement axis that is different from the first distance;
selectively adjusting a rotational speed of each transfer puck as the transfer pucks are rotated between a pick-up location located adjacent the web and an application location located adjacent the substrate; and
rotating a pair of transfer pucks including the first transfer puck and the second transfer puck such that the second transfer puck is spaced a first circumferential distance from the first transfer puck at the application location, and adjacent transfer puck pairs being spaced a second circumferential distance at the application location that is less than the first circumferential distance.

* * * * *